US006210908B1

(12) United States Patent
Annunziato et al.

(10) Patent No.: US 6,210,908 B1
(45) Date of Patent: Apr. 3, 2001

(54) ACTIVATED PEPTIDES AND CONJUGATES

(75) Inventors: Michael E. Annunziato, Mansfield; Paul S. Palumbo, West Newton, both of MA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/388,664

(22) Filed: Sep. 2, 1999

Related U.S. Application Data

(62) Division of application No. 08/833,546, filed on Nov. 11, 1998, now Pat. No. 5,977,299.

(51) Int. Cl.$^7$ ...................... G01N 33/543; G01N 33/553; C12N 9/96; C07K 11/02; C07K 17/02

(52) U.S. Cl. .................................. 435/7.1; 435/4; 435/5; 435/7.1; 435/7.93; 435/188; 435/527; 435/7.92; 435/97.4; 436/527; 436/529; 436/532; 436/530; 530/391.1; 530/391.9; 530/395; 530/405; 530/317; 530/402; 530/403; 530/324; 530/325; 530/326; 530/323; 530/14; 530/13; 530/12; 514/11

(58) Field of Search ................................. 435/4, 5, 7, 7.1, 435/793, 188, 527, 7.92, 974; 436/527, 529, 532, 530; 530/391.1, 391.9, 395, 405, 317, 402–403, 324–326, 323, 14, 13, 12; 405/403, 402; 514/11

(56) References Cited

U.S. PATENT DOCUMENTS

| 5,066,782 | 11/1991 | Montagnier et al. |
| 5,294,536 | 3/1994 | Palumbo . |
| 5,574,132 | 11/1996 | Lacroix . |
| 5,977,299 | * 11/1999 | Annunziato et al. .................. 530/317 |

OTHER PUBLICATIONS

G.A. Koppel; *Bioconjugate Chem.*; "Recent Advances with Monoclonal Antibody Drug Targeting for the Treatment of Human Cancer"; 1:13 (1990).

C–H Tung, et al.; *Bioconjugate Chem.*; "Preparation of Oligonucleotide–Peptide Conjugates"; 2:464 (1991).

M.E. Annunziato, et al.; *Bioconjugate Chem.* "ρ–Maleimidophenyl Isocyanate: A Novel Heterobifunctional Linker for Hydroxyl to Thiol Coupling"; 4:212 (1993).

K. Ara, et al.; *Tetrahedron Letters*; "Synthesis of Oligonucleotide–Peptide Conjugates Containing a KDEL Signal Sequence", 34;50: 8087 (1993).

K.M. Wilson, et al.; *Journal of Immunological Methods*; "Simplified Conjugation Chemistry for Coupling Peptides to F(ab') Fragments: Autologous Red Cell Agglutination Assay for HIV–1 Antibodies"; 175:267 (1994).

K. Arar, et al.; *Bioconjugate Chem.*; "Synthesis and Antiviral Activity of Peptide–Oligonucleotide Conjugates Prepared by Using Nα–(Bromoacetyl)peptides"; 5:573 (1995).

R. Wetzel, et al.; *Bioconjugate Chem.*; "A general method for highly selective cross–linking of unprotected polypeptides via pH–controlled modification of N–terminal alpha–amino groups"; 1:114–122 (1990).

D.S. Jones, et al.; *Bioconjugate Chem.*; "Conjugates of double–stranded oligonucleotides with poly(theylene glycol) and keyhole limpet hermocyanin: A model for treating systemic lupus erythematosus"; 5:390–399 (1994).

R.E. Galardy, et al.; *J. Biol. Chem.*; "Photoaffinity labelling of peptide hormone binding sites"; 249:3510–3518 (1974).

C.W.T. Yeung, et al.; *Biochemistry*, "Photoaffinity labeling of insulin receptor with an insulin analog selectively modified at the amino terminal of the β–chain"; 19:2196–2203 (1980).

C.C. Yip, et al.; *Biochemistry*, "Photoaffinity labeling of insulin receptor proteins of liber plasma membrane preparations"; 17:70–76 (1980).

J. Massague, et al.; *J. Biol. Chem.*; Identification of a nerve growth factor receptor protein in sympathetic ganglia membranes by affinity labeling; 256:9419–9424 (1981).

I. Ji, et al.; *Proc. Natl. Acad. Sci. USA*; "Both α and β subunits of umann choriogonadotropin photoaffinity label the hormone receptor"; 78:5465–5469 (1981).

Johnson, et al; *Proc. Natl. Acad. Sci. USA*; "Identification of the glucagon receptor in rat liver membranes by photoaffinity crosslinking"; 78:8750878 (1981).

Baallmer–Hofer, et al.; *Anal. Biochem.*; "Isolation of in situ crosslinked ligand–receptor complexes using an anti-crosslinker specific antibody"; 126:246–250 (1982).

R.R. Goewert, et al.*Biochemistry*; "Calmodulin binding to rat adipocyte plasma membrane: characterization and photoaffinity crosslinking of calmodulin to binding proteins"; 21:5310–5315 (1982).

R.L. Vandlen, et al.; *J. Biol. Chem.*; "Identification of receptor for atrial natruiuretic factor in rabit aorta membranes by affinity cross–linking"; 260:10889–10892 (1985).

C.L. Wood, et al.;*J. Biol. Chem.*; "Covalent cross–linking of vasoactive intestinal polypeptide to its receptors on intact human lymphoblasts" 260:1243–1247 (1985).

Nissenson, et al.*biochemistry*; "Covalent Labeling of a high–affinity, guanyl nucleotide sensitive parathyroid hormone receptor in canine renal cortex"; 26:1874–1878 (1987).

(List continued on next page.)

*Primary Examiner*—Long V. Le
*Assistant Examiner*—Lisa V. Cook
(74) *Attorney, Agent, or Firm*—Linda M Buckley; Robert L Buchanan; Lois K Ruszala

(57) ABSTRACT

Novel activated peptides and conjugates thereof, useful in diagnostic assays and therapeutics, and processes for the preparation thereof are disclosed.

16 Claims, No Drawings

OTHER PUBLICATIONS

Narciandi, et al.; *J. Chem. Tech. Biotechnol.*; "Production and Purfication of a Fused Recombinant Protein gp–36 (HIV–2) from *Escherichia coli*"; 66:1–6 (1996).

K. Arar, et al., Tetrahedron Letters, 34, No. 50, 8087 (1993) published in Great Britain and entitlea "Synthesis of Oligonucleotide–Peptide Conjugates Containing a KDEL Signal Sequence".

K. M. Wilson, et al., Journal of Immunological Methods 175, 267 (1994) published in the Netherlands and entitled "Simplified Conjugation Chemistry for Coupling Peptides Peptides to F(ab') Fragments: Autologous Red Cell Agglutination Assay for HIV–1 Antibodies".

K. Arar, et al., Bioconjugate Chem., 6, 573 (1995) published in the United States and entitled "Synthesis and Antiviral Activity of Peptide–Oligonucleotide Conjugates Prepared by Using $N\alpha$–(Bromoacetly)peptides".

G. A. Koppel, Bioconjugate Chem., 1, 13 (1990) published in the U.S. and entitled "Recent Advances with Monoclonal Antibody Drug Targeting for the Treatment of Human Caner".

C.–H. Tung, et al., Bioconjugate Chem., 2, 464 (1991) published in the U.S. and entitled "Preparation of Oligonucleotide–Peptide Conjugates".

M. E. Annunziato, et al., Bioconjugate Chem., 4, 212 (1993) published in the U.S. and entitled "p–Maleimidophenyl Isocyanate: A Novel Heterobifunctional Linker for Hydroxy to Thio Coupling".

K. Arar, et al. Tetrahedron Letters, 34, No. 50, 8087 (1993) published in Great Britain and entitled "Synthesis Oligonucleotide–Peptide Conjugates Containing a KDEL Signal Sequence".

R. Wetzel, R. Halualani, J. T. Stults and C. Quan. A general method for highly selective cross–linking of unprotected polypeptides via pH–controlled modification of N–terminal alpha–amino groups. *Bioconjugate Chem.* 1: 114–122 (1990).

D. S. Jones, J. P. Hachmann, S. A. Osgood, M. S. Hayag, P. A. Barstad, G. M. Iverson and S. M. Coutts. Conjugates of double–stranded oligonucleotides with poly(ethylene glycol) and keyhole limpet hemocyanin: A model for treating systemic lupus erythematosus. *Bioconjugate Chem.* 5: 390–399 (1994).

R. E. Galardy, L. C. Craig, J. D. Jamieson and M. P. Printz. Photoaffinity labeling of peptide hormone binding sites. *J. Biol. Chem.* 249: 3510–3518 (1974).

C. W. T. Yeung, M. L. Moule and C. C. Yip. Photoaffinity labeling of insulin receptor with an insulin analog selectively modified at the amino terminal of the B–chain. *Biochemistry* 19: 2196–2203 (1980).

C. C. Yip, C.W.T. Yeung and M. L. Moule Photoaffinity labeling of insulin receptor proteins of liver plasma membrane preparations. *Biochemistry* 19: 70–76 (1980).

J. Massague, B. J. Guillette, M. P. Czech, C. J. Morgan and R. A. Bradshaw. Identification of a nerve growth factor receptor protein in sympathetic ganglia membranes by affinity labeling. *J. biol. Chem.* 256: 9419–9424 (1981).

I. Ji and T. H. Ji. Both a and b subunits of umann choriogonadotropin photoaffinity label the hormone receptor. *Proc. Natl. Acad. Sci. USA* 78: 5465–5469 (1981).

G. L. Johnson, V. L. MacAndrew, Jr., and P. F. Pilch. Identification of the glucagon receptor in rat liver membranes by photoaffinity crosslinking. *Proc. Natl. Acad. Sci. USA* 78: 875–878 (1981).

K. Ballmer–Hofer, V. Schlup, P. Burn ad M. M Burger. Isolation of in situ crosslinked ligane–receptor complexes using an anticrosslinker specific antibody. *Anal. Biochem.* 126: 246–250 (1982).

R. R. Goewert, M. Landt and J. M. McDonald. Calmodulin binding to rat adipocyte plasma membrane: Characterization and photoaffinity crosslinking of calmodulin to binding proteins. *Biochemistry*0 21: 5310–5315 (1982).

R. L. Vandlen, K. E. Arcuri and M. A. Napier. Identification of a receptor for atrial natriuretic factor in rabbit arota membranes by affinity cross–linking. *J. Biol. Chem.* 260: 10889–10892 (1985).

C. L. Wood and M. S. O'Dorisio. Covalent cross–linking of vasoactive intestinal polypeptide to its receptors on intact human lymphoblasts. *J. Biol. Chem.* 260: 1243–1247 (1985).

R. A. Nissenson, D. Karpf, T. Bambino, J. Winer, M. Canga, K. Nyiredy and C. D. Arnaud. Covalent Labeling of a high–affinity, guanyl nucleotide sensitive parathyroid hormone receptor in canine renal cortex. *Biochemistry* 26: 1874–1878 (1987).

M. E. Annunziato, et al., Bioconjugate Chem., 4, 212 (1993) published in the U.S. and entitled "p–Maleimidophenyl Isocyanate: A Novel Heterobifunctional Linker for Hydroxyl to Thio Coupling".

\* cited by examiner

ACTIVATED PEPTIDES AND CONJUGATES

CROSS-REFERENCE TO RELATED APPLICATION

The present application is a divisional application of U.S. Ser. No. 08/833,546 filed Nov. 11, 1998 now U.S. Pat. No. 5,977,299, the disclosure of which is incorporated herein by reference.

FIELD OF THE INVENTION

The present invention relates to activated peptides, conjugates and methods of preparation thereof, and their use in diagnostic assays and therapeutics.

BACKGROUND OF THE INVENTION

Numerous assays have been developed for the detection and determination of proteins, e.g., antibodies in biological fluids. One class, the immunoassays, which has evolved into an invaluable tool in diagnostics, is based upon the principle of specific binding of antibodies to haptens and/or antigens. In a typical immunoassay, a test sample, containing an analyte of interest, and an antibody, to which it specifically binds, are incubated, and then washed to separate free and bound analytes. An enzyme-labeled antibody that recognizes the resulting complex is added, incubated, and washed, and finally substrate, an enzyme detection system, is added and the labeled complex is detected and determined.

Conjugates of peptides specific to antibodies have been used advantageously in immunoassays. Conjugates of peptide analogues of viral proteins, that is, segments of the proteins bearing the epitopic sequence, for example, of the human immunodeficiency viruses (HIV) and labeled enzymes linked through a maleiimide moiety have been described as being particularly advantageous in the detection and determination of antibodies to HIV. See U.S. Pat. No. 5,294,536 granted to Paul S. Palumbo on Mar. 15, 1994 ('536-patent). The conjugates of activated peptides, prepared by the processes described in the '536- patent are not homogenous, the activated peptides being derived from the terminal amino group and/or the internal amino and hydroxyl groups of the peptide analogue. Interaction of the internal amino and/or hydroxyl groups of the peptide analogue and the crosslinking agent, in addition to that of the terminal amino group, diminishes the effectiveness of the epitopic centers of the peptide analogue thereby reducing the sensitivity of the assay for the detection and determination of specific binding antibodies. For example, interaction of the amino group of the lysine subunit and/or the amino and the hydroxy subunits of the serine subunit of the epotopic segment of the peptide analog of the HIV virus and the crosslinker reduces the sensitivity of the immunoassay for the detection or determination of antibodies to HIV, the greater the interaction of the internal amino and/or hydroxyl group relative to the terminal amino group, the lower the sensitivity of the assay. The processes for the preparation of activated peptides 3 and conjugates 5 described in the aforementioned '536-patent involve condensation of an isocyanatomaleiimide 1

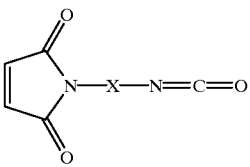

wherein X is a spacer group with a peptide having a terminal amino group of formula 2

$$RNH_2 \qquad 2$$

wherein R is the remainder of the peptide to form an activated peptide 3

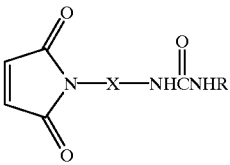

wherein R and X are as above, which is then condensed with a thiolated enzyme of formula 4

$$R_1SH \qquad 4$$

wherein $R_1$ is the remainder of an enzyme to form a conjugate of formula 5

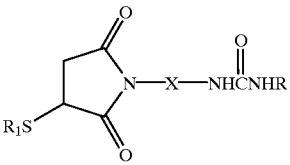

Wherein X, R, and $R_1$ are as defined herein. The critical step in the process, the reaction of the crosslinker 1 with a peptide 2, characterized by the presence of a terminal amino group and internal amino and/or hydroxyl groups, affords an activated peptide 1 derived from the terminal amino group, as well as activated peptides derived from the internal amino and/or hydroxyl groups of the peptide, and combinations thereof.

SUMMARY OF THE INVENTION

It has now been found that by performing the reaction of the isocyanatomaleiimide 1 with a peptide 2 as a salt of a strong protonic acid, the activated peptide is formed substantially free of activated peptides derived from internal amino and/or hydroxyl groups, e.g., of serine or lysine, i.e., the reaction takes place almost exclusively at the terminal amino group of the peptide 2 to regiospecifically form an activated peptide 3 with the epitopic segment of the peptide 2 essentially intact.

It has now also been found that the integrity of the binding region of the activated peptide 3 is maintained in the conjugate 5 and that use of the essentially homogeneous conjugate 5 of the invention in an immunoassay results in a marked improvement of the sensitivity of the assay.

DETAILED DESCRIPTION OF PREFERRED EMBODIMENTS

More particularly, the present invention relates to activated peptides of formula 3

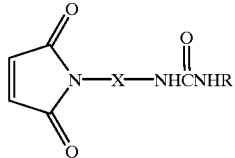

3 wherein X is loweralkylene, an aromatic carbocyclic moiety or a saturated carbocyclic moiety and R is the remainder of a peptide having a terminal primary amino group and free internal hydroxyl and/or amino groups, useful for the preparation of conjugates 5

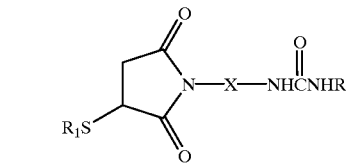

5 wherein R and X are as defined above and $R_1$ is the remainder of an enzyme having a free thiol group, useful for the detection and determination of antibodies in samples of interest related to the human immunodeficiency viruses.

Preferred activated peptides 3 are those wherein X is an aromatic moiety; most preferred are peptides wherein X is phenyl, and R is the remainder of a peptide analogue having a terminal amino group selected from the group consisting of a. GLY-CYS-SER-GLY-LYS-LEU-ILE-CYS-THR-THR-ALA-VAL-PRO-TRP-ASN-ALA-SER (SEQ ID NO: 1);
      ⌐─────────────────⌐ b. ARG-VAL-THR-ALA-ILE-GLU-LYS-TYR-LEU-GLN-ASP-GLN-ALA-
ARG-LEU-ASN-SER-TRP-GLY-CYS-ALA-PHE-ARG-GLN-VAL-CYS-HIS-THR-THR-VAL-PRO-TRP-VAL-ASN-ASP-SER (SEQ ID NO: 2);

c. ASP-GLN-ALA-ARG-LEU-ASN-SER-TRP-GLY-
CYS-ALA-PHE-ARG-GLN-VAL-CYS-HIS-THR-THR-VAL-PRO-TRP-VAL-ASN (SEQ ID NO: 3);

d. ASN-GLN-GLN-ARG-LEU-ASN-LEU-TRP-GLY-
CYS-LYS-GLY-LYS-LEU-ILE-CYS-TYR-THR-SER-VAL-LYS-TRP-ASN (SEQ ID NO: 4);

e. ARG-ILE-LEU-ALA-VAL-GLU-ARG-TYR-LEU-LYS-ASP-GLN-GLN-
LEU-LEU-GLY-ILE-TRP-GLY-CYS-SER-GLY-LYS-LEU-ILE-CYS-THR-THR-ALA-VAL-PRO-TRP-ASN-ALA-SER (SEQ ID NO: 5);

f. LYS-ILE-LEU-ALA-VAL-GLU-ARG-TYR-LEU-LYS-ASP-GLN-GLN-
LEU-LEU-GLY-ILE-TRP-GLY-CYS-SER-GLY-LYS-LEU-ILE-CYS-THR-THR-ALA-VAL-PRO-TRP-ASN-ALA-SER-GLY-LYS-LEU-ILE- (SEQ ID NO: 6);

g. ASP-GLN-GLN-LEU-LEU-GLY-ILE-TRP-GLY-
CYS-SER-GLY-LYS-LEU-ILE-CYS-THR-THR-ALA-VAL-PRO-TRP-ASN (SEQ ID NO: 7);

h. ASN-GLN-GLN-SER-ARG-TRP-GLY-LEU-GLY-SER-PRO-ASN-
CYS-HIS-GLY-PRO-ASP-TRP-ALA-SER-PRO-VAL-CYS-GLN-ARG-HIS-SER (SEQ ID NO: 8); and i. LYS-ILE-GLU-PRO-LEU-GLY-VAL-ALA-PRO-THR-LYS-ALA-LYS-ARG-ARG-VAL-VAL-GLN-ARG-GLU-LYS-ARG (SEQ ID NO: 9).

As used throughout the specification and appended claims, the term alkylene refers to a saturated straight or branched chain hydrocarbon having 1 to 10 carbon atoms. Examples of alkylene groups are methylene (—CH$_2$—), ethylene (—CH$_2$CH$_2$—), butylene

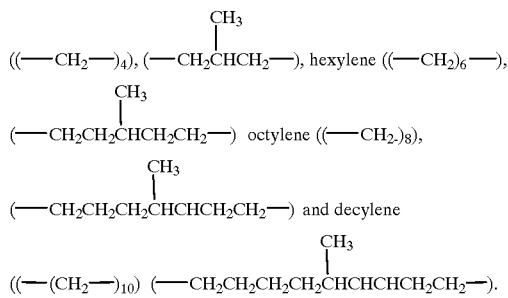

The term "lower" as applied to alkylene groups refers to a carbon skeleton having 1 to 6 carbon atoms.

The term "alpha-amino acid" refers to a compound characterized by the presence of a carboxylic acid group and an alpha-amino group bound to the same carbon atom

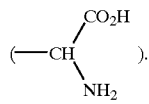

Examples of amino acids are alanine, valine, leucine, isoleucine, proline (or hydroxyproline), phenylalanine, tryptophan, methionine, glycine, serine, threonine, cysteine, tyrosine, asparagine, glutamine, aspartic acid, glutamic acid, lysine, arginine, and histidine.

The term "peptide" refers to polymers of two or more amino acids linked covalently through the carboxyl group of an amino acid and the amino group of another with the elimination of water. Examples of peptides are those compiled herein in the Sequence Listing.

The term "protein" refers to a macromolecule of one or more chains of amino acids bound covalently through peptide bonds

Proteins include enzymes, antibodies, antigens, peptides and the like.

The term "hapten" refers to a low-molecular-weight compound that reacts specifically with an antibody, but does not stimulate antibody production unless complexed with a carrier protein.

The term "antigen" refers to a substance or entity (usually a protein) that induces the direct production of antibodies.

The term "spacer group" refers to a moiety bridging the isocyanato and maleiimides groups and linking the protein and thiolated enzyme moieties of a conjugate. Examples of spacer groups are alkylene (hereindefined), aromatic carbocyclics, such as phenyl or naphthyl optionally having an alkylene group for attachment to the maleiimide moiety and dimethylamino, methoxy, ethoxy, methyl, ethyl, sulfonamido, sulfonic acid substituents, and saturated carbocyclics such as cyclohexyl, cyclohexylalkyl, cyclopentyl, cyclopentylalkyl, cycloheptyl, cycloheptylalkyl.

The term "regiospecific" refers to a process in which one specific structural or positional isomer is formed to the essential exclusion of other possible isomers.

The term "remainder" as applied to peptides refers to the moiety bound to the terminal amino group thereof, for example, the terminal amino group of the terminal glycine moiety of the sequence of amino acids shown below:

(SEQ ID NO: 1)

GLY-CYS-SER-GLY-LYS-LEU-ILE-CYS-THR-THR-ALA-VAL-PRO-TRP-ASN-ALA-SER

The term "remainder" as applied to an enzyme having a free thiol group refers to the moiety bound to the thiol group thereof, for example, specific enzymes such as beta-D-galactosidase, peroxidase, glucose oxidase and alkaline phosphatase, in which a thiol group has been introduced.

The N-terminal activated peptides 3 of the present invention are prepared by contacting an isocyanatomaleiimide 1 with a peptide 2, as a salt of a strong protonic acid, having in the remainder free amino and/or hydroxyl groups capable of interaction with the isocyanato moiety of the crosslinker 1, in a suitable solvent, conditions under which the terminal amino group regioselectively reacts with the isocyanato moiety of the crosslinker 1, without substantial interaction of the internal amino and/or hydroxyl groups with the isocyanato moiety. Included among strong protonic acids are hydrohalic acids such as hydrobromic acid and hydrochloric acid. Also included among such acids are haloacetic acids, for example, trichloroacetic and trifluoroacetic acid. Haloacetic acids are preferred. Trifluoroacetic acid is most preferred.

A variety of peptides 2 containing a terminal amino moiety are commercially available, many as salts of trifluoroacetic acid. In the event the peptide 2 is not available as the trifluoroacetic acid salt, hydrohalic and haloacetic acid salts may be prepared by conventional methods.

Suitable solvents include dipolar aprotic solvents, for example, dimethylformamide, dimethylacetamide, hexamethylphosphoramide, or dimethylsulfoxide. Dimethylformamide is the preferred solvent.

The reaction of a terminal amino group of a peptide 2 with a crosslinker 1 is carried out at a temperature compatible with the stability of the reactants, generally as determined by the stability of the peptide 2. Typically, the reaction is performed at about 30° C.

The relative amounts of the peptide 2 and crosslinker 1 are not critical. With about a threefold excess of crosslinker 1 to peptide 2, good yields of the activated peptide 3 are obtained.

The reaction of a peptide 2 and crosslinker 1 is worked up by conventional methods and the product is purified by known chromatographic techniques, for example, reverse phase high performance liquid chromatography.

The activated peptide 2 was analyzed by various spectral techniques, for example, mass spectrometry; and the regiospecifity of reaction of the crosslinker 1 with the N-terminal amino group of the peptide 2 was established by aminopeptidase and trypsin digestion in combination with mass spectral analyses. See, for example, K. Arar, et al., Tetrahedron Letters, 34, 8087 (1993), ref 15, and B. Keil in The Enzymes, P. D. Boyer, Editor, Vol. III, Academic Press, New York, N.Y., 1971, Chapter 8, for a discussion of these methods of determining the site of reaction of a peptide having multiple amino and/or hydroxyl groups with a crosslinker such as an isocyanatomaleiimide 1.

The yields of the activated peptide 3 of the present invention prepared by the reaction of an isocyanatomaleiimide 1 with a peptide 2 are uniformly high, the crude yields by chromatographic techniques falling within the range of about 49 to about 91%, the isolable yields falling within the range of about 47 to about 60%.

The purity of the activated peptides 3, the condensation products of isocyanatomaleiimides 1 and N-terminal peptides 2, was established by reverse phase high performance liquid chromatography.

The conjugates 5 of the present invention are usefull in enzyme-linked immunoassays (ELISA) for the detection and determination of proteins, e.g., antibodies, particularly antibodies to human immunodeficiency viruses in a ELISA module of the OPUS4 system. See H. J. Crowley and M. A. Bandin in The Immunoassay Handbook, D. Wild, Edition, Stockton Press, New York, N.Y., 1994, page 197. In such an assay, e.g., an analyte of interest of a biological sample, e.g., an antibody, and the conjugate are incubated, applied to antibody capturing support, washed with a substrate, incubated and detected. In particular, the sample of interest containing an antibody to a human immunodeficiency virus and the conjugate of a peptide derived from a glycoprotein of a human immunodeficiency virus are incubated, applied to a matrix of a fusion protein, washed with methyl umbelliferyl phosphate, incubated, and the amount of conjugate bound to the peptide specific antibody is detected and determined by fluorimetry.

Enzymes that contain a thiol group such as β-D-galactosidase and those that do not such as peroxidase, glucose oxidase and alkaline phosphatase, into which a thiol may be introduced, can be employed in the conjugation with activated peptides.

The activated peptides 3 of the present invention are also useful as therapeutics for the treatment of disease. See K. Arar, ibid., page 1 and references cited thereon, as well as Gary A. Koppel, Bioconjugate Chemistry, 1, 13 (1990).

The peptide starting materials are available from commercial sources.

The invention will now be further described with respect to specific preferred embodiments by way of examples, it being understood that these are intended to be illustrative only and the invention is not limited to the materials, processes, etc., recited therein.

EXAMPLE 1

N-Terminal Activation of Peptide BC202 (Seq ID No: 2) with p-Maleiimidebenzene isocyanate. Synthetic peptide BC202 (Seq ID No: 2), consisting of 36 amino acids with an internal disulfide loop is derived from HIV-2 genome and is a portion of the envelope protein gp36. An N-terminal arginine, internal lysine and serine, and a C-terminal serine are potential sites for activation with p-maleiimidebenzene isocyanate (PMBI). In this example, 7.1 mg of the trifloroacetic acid salt of BC202 was dissolved in 1.42 ml of dry dimethylformamide. To the solution a 3-molar excess (1.09 mg) of p-maleiimidebenzene isocyanate in 0.109 ml of dimethylformamide was added. The reaction mixture was incubated for 30 mins at 30° C., incubated with 4.59 ml of deionized water for 5 mins at 30° C., and centrif uged. The precipitate was collected, and the mother liquor was purified by reverse phase high performance liquid chromatography with a linear gradient of 30%–35% acetonitrile in 0.06% trifluoroacetic over 30 mins. The flow rate was 4.7 ml/min and the separation monitored at 220 nm and 280 nm. The appropriate fractions were collected and evaporated. The residue was dried to yield the activated peptide as a powder; yield 94% by high performance liquid chromatography, 60% by isolation.

The activated peptide was analyzed by mass spectrometry, aminopeptidase digestion, trypsin digestion in combination with mass spectrometry, back titration with mercaptoethanol and reaction with 5,5'-dithiobis(2-nitrobenzoic acid) and conjugated to alkaline phosphatase for functional testing in an HIV-2 assay.

The reaction and separation conditions for the preparation of the activated peptide of the invention, prepared by processes substantially similar to those as described in the example, and the yields of the products so obtained are summarized in the Table.

TABLE

| Peptide* | PMBI (molar ratio) | Separation Conditions and Eluent ** | Activated Peptide % Yield by HPLC (Isolation Yield) |
| --- | --- | --- | --- |
| D-23-N (SEQ ID NO:7) | 3X | Isocratic 30% B | ND |
| D-24-N (SEQ ID NO:3) | 3X | Isocratic 30% B | 90 |
| N-23-N (SEQ ID NO:4) | 3X | Isocratic 30% B | 86% (50%) |
| BC80 (SEQ ID NO:1) | 10X | Isocratic 30% B | 89% (60%) |
| BC80 (SEQ ID NO:1) | 3X | Isocratic 30% B | 77% |
| BCH132 (SEQ ID NO:9) | 3X | Gradient 15-30% B 30 min. | 47% |
| BCH4O8 (SEQ ID NO:6) | 3X | Gradient 30-40% B 30 min. | 91% |
| BCHI78 (SEQ ID NO:8) | 20X | Isocratic 25% B | 87% |
| BC202 (SEQ ID NO:2) | 3X | Gradient 30-35% B 30 min. | 94% (60%) |
| BCH87 (SEQ ID NO:5) | 3X | Gradient 32-37% B 30 min. | 74% (49%) |

(%) Represents isolation yields after pooling and drying. Each value is a mean of two runs.
*Source
D-23-N (SEQ ID NO:7), Neosystems S.A., Strasbourg, France;
D-24-N (SEQ ID NO:3), Neosystems S.A., Strasbourg, France;
N-23-N (SEQ ID NO:4), Neosystems S.A., Staasbourg, France;
BC 80 (SEQ ID NO: 1), BioChem Immunosystems Inc., Montreal, Canada;
BCH 132 (SEQ ID NO:9), BioChem Immunosystems Inc., Montreal, Canada;
BCH 408 (SEQ ID NO:6), BioChem Immunosystems Inc., Montreal, Canada;
BCH 178 (SEQ ID NO:8), BioChem Immunosystems Inc., Montreal, Canada;
BC 202 (SEQ ID NO:2), BioChem Immunosystems Inc., Montreal, Canada; and
BCH 87 (SEQ ID NO:5), BioChem Immunosystems Inc., Montreal, Canada.
**Chromatography Eluent
30% B - a solution of 30% by volume of a solution of 0.06% by volume of trifluoroacetic acid in acetonitrile and 70% by volume of a solution of 0.06% of trifluoroacetic acid in deionized water.
15% B - a solution of 15% by volume of a solution of 0.06% by volume of trifluoroacetic acid in acetonitrile and 85% by volume of a solution of 0.06% of trifluoroacetic acid in deionized water.
25% B - a solution of 25% by volume of a solution of 0.06% by volume of trifluoroacetic acid in acetonitrile and 75% by volume of a solution of 0.06% of trifluoroacetic acid in deionized water.
32% B - a solution of 32% by volume of a solution of 0.06% by volume of trifluoroacetic acid in acetonitrile and 68% by volume of a solution of 0.06% of trifluoroacetic acid in deionized water.
35% B - a solution of 35% by volume of a solution of 0.06% by volume of trifluoroacetic acid in acetonitrile and 65% by volume of a solution of 0.06% of trifluoroacetic acid in deionized water.
37% B - a solution of 37% by volume of a solution of 0.06% by volume of trifluoroacetic acid in acetonitrile and 63% by volume of a solution of 0.06% of trifluoroacetic acid in deionized water.
40% B - a solution of 40% by volume of a solution of 0.06% by volume of trifluoroacetic acid in acetonitrile and 60% by volume of a solution of 0.06% of trifluoroacetic acid in deionized water.

SEQUENCE LISTING (1) GENERAL INFORMATION:

(iii) NUMBER OF SEQUENCES:  9

(2) INFORMATION FOR SEQ ID NO: 1:

(i) SEQUENCE CHARACTERISTICS:
        (A) LENGTH:  17 amino acids
        (B) TYPE:  amino acid
        (C) STRANDEDNESS: single
        (D) TOPOLOGY:  linear (xi) SEQUENCE DESCRIPTION:  SEQ ID NO: 1:

GLY CYS SER GLY LYS LEU ILE CYS THR THR ALA VAL PRO TRP ASN ALA
1               5                   10                  15

SER (2) INFORMATION FOR SEQ ID NO: 2:

(i) SEQUENCE CHARACTERISTICS:
        (A) LENGTH:  36 amino acids
        (B) TYPE:  amino acid
        (C) STRANDEDNESS: single
        (D) TOPOLOGY:  linear (xi) SEQUENCE DESCRIPTION:  SEQ ID NO: 2:

ARG VAL THR ALA ILE GLU LYS TYR LEU GLN ASP GLN ALA ARG LEU ASN
1               5                   10                  15

SER TRP GLY CYS ALA PHE ARG GLN VAL CYS HIS THR THR VAL PRO TRP
            20                  25                  30

VAL ASN ASP SER
        35

(2) INFORMATION FOR SEQ ID NO: 3:

(i) SEQUENCE CHARACTERISTICS:
        (A) LENGTH:  24 amino acids
        (B) TYPE:  amino acid
        (C) STRANDEDNESS: single
        (D) TOPOLOGY:  linear (xi) SEQUENCE DESCRIPTION:  SEQ ID NO: 3:

ASP GLN ALA ARG LEU ASN SER TRP GLY CYS ALA PHE ARG GLN VAL CYS HIS
1               5                   10                  15

THR THR VAL PRO TRP VAL ASN
        20

(2) INFORMATION FOR SEQ ID NO: 4:

(i) SEQUENCE CHARACTERISTICS:
        (A) LENGTH:  23 amino acids
        (B) TYPE:  amino acid
        (C) STRANDEDNESS: single
        (D) TOPOLOGY:  linear (xi) SEQUENCE DESCRIPTION: SEQ ID NO: 4:

ASN GLN GLN ARG LEU ASN LEU TRP GLY CYS LYS GLY LYS LEU ILE CYS
1               5                   10                  15

TYR THR SER VAL LYS TRP ASN
        20

(2) INFORMATION FOR SEQ ID NO: 5:

(i) SEQUENCE CHARACTERISTICS:
    (A) LENGTH: 35 amino acids
    (B) TYPE: amino acid
    (C) STRANDEDNESS: single
    (D) TOPOLOGY: linear (xi) SEQUENCE DESCRIPTION: SEQ ID NO: 5:

```
ARG ILE LEU ALA VAL GLU ARG TYR LEU LYS ASP GLN GLN LEU LEU GLY
1               5                   10                  15

ILE TRP GLY CYS SER GLY LYS LEU ILE CYS THR THR ALA VAL PRO TRP
            20                  25                  30

ASN ALA SER
        35
```

(2) INFORMATION FOR SEQ ID NO: 6:

(i) SEQUENCE CHARACTERISTICS:
        (A) LENGTH: 39 amino acids
        (B) TYPE: amino acid
        (C) STRANDEDNESS: single
        (D) TOPOLOGY: linear (xi) SEQUENCE DESCRIPTION: SEQ ID NO: 6:

```
LYS ILE LEU ALA VAL GLU ARG TYR LEU LYS ASP GLN GLN LEU LEU GLY
1               5                   10                  15

ILE TRP GLY CYS SER GLY LYS LEU ILE CYS THR THR ALA VAL PRO TRP
            20                  25                  30

ASN ALA SER GLY LYS LEU ILE
        35
```

(2) INFORMATION FOR SEQ ID NO: 7:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 7:

```
ASP GLN GLN LEU LEU GLY ILE TRP GLY CYS SER GLY LYS LEU ILE CYS
1               5                   10                  15

THR THR ALA VAL PRO TRP ASN
            20
```

(2) INFORMATION FOR SEQ ID NO: 8:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 8:

```
ASN GLN GLN SER ARG TRP GLY LEU GLY SER PRO ASN CYS HIS GLY PRO
1               5                   10                  15

ASP TRP ALA SER PRO VAL CYS GLN ARG HIS SER
            20                  25
```

(2) INFORMATION FOR SEQ ID NO: 9:

(i) SEQUENCE CHARACTERISTICS:
        (A) LENGTH: 22 amino acids
        (B) TYPE: amino acid
        (C) STRANDEDNESS: single -continued

```
        (D) TOPOLOGY:  linear (xi) SEQUENCE DESCRIPTION:  SEQ ID NO: 9:

LYS ILE GLU PRO LEU GLY VAL ALA PRO THR LYS ALA LYS ARG ARG VAL
1               5                   10                  15

VAL GLN ARG GLU LYS ARG
            20
```

We claim:

1. A solid support for use in immunoassays comprising a compound of the formulae

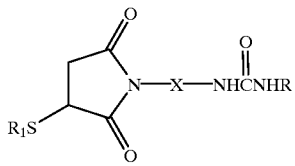

wherein X is loweralkylene, an aromatic carbocyclic group or a saturated carbocyclic group and R is the remainder of a peptide having a terminal amino group and characterized by the presence of internal amino and/or hydroxyl groups, in which the terminal amino group is bound to the carbon atom of the amide carbonyl group of the compound, the compound being substantially free of activated peptides in which at least one of the internal amino and/or hydroxy groups is bound to the carbon atom of the amide carbonyl group; and $R^1$ is the remainder of a compound characterized by the presence of a thiol group bound thereby to the 3-position of the maleiimide moiety.

2. A method of determining an analyte in a sample of interest comprising the steps of:
   a. incubating a sample of interest with solid support comprising a compound of the formula

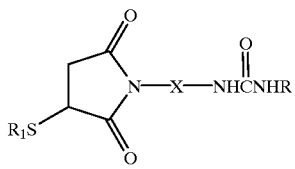

wherein X is a loweralkylene, an aromatic carbocyclic group or a saturated carbocyclic group and R is the remainder of a peptide having a terminal amino group and characterized by the presence of internal amino and/or hydroxyl groups, the compound being substantially free of activated peptides in which at least one of the internal amino and/or hydroxyl groups is bound to the carbon atom of the amide carbonyl group of the compound; and $R_1$ is the remainder of a compound characterized by the presence of a thiol group bound thereby to the 3-position of the maleiimide moiety to provide an analyte/conjugate mixture;
   b. washing the analyte/conjugate mixture with a substrate from an analyte/conjugate/substrate mixture;
   c. incubating the analyte/conjugate/substrate mixture; and
   d. measuring the amount of analyte bound to the mixture as being indicative of the amount of analyte in the sample of interest.

3. A method of claim 2 wherein X is an aromatic carbocyclic group.

4. A method of claim 3 wherein X is phenyl.

5. The method according to claim 4 wherein R is the remainder of a peptide having a terminal amino group of the formula (SEQ ID NO: 1)

GLY-CYS-SER-GLY-LYS-LEU-ILE-CYS-THR-THR-ALA-VAL-PRO-TRP-ASN-ALA-SER.

6. The method according to claim 2 wherein R is the remainder of a peptide having a terminal amino group of the formula (SEQ ID NO: 2)

ARG-VAL-THR-ALA-ILE-GLU-LYS-TYR-LEU-GLN-ASP-GLN-ALA-ARG-LEU-ASN-SER-TRP-GLY-CYS-ALA-PHE-ARG-GLN-VAL-CYS-HIS-THR-THR-VAL-PRO-TRP-VAL-ASN-ASP-SER.

7. The method according to claim 2 wherein R is the remainder of a peptide having a terminal amino group of the formula (SEQ ID NO: 3)

ASP-GLN-ALA-ARG-LEU-ASN-SER-TRP-GLY-CYS-ALA-PHE-ARG-GLN-VAL-CYS-HIS-THR-THR-VAL-PRO-TRP-VAL-ASN.

8. The method according to claim 2 wherein R is the remainder of a peptide having a terminal amino group of the formula (SEQ ID NO: 4)

ASN-GLN-GLN-ARG-LEU-ASN-LEU-TRP-GLY-CYS-LYS-GLY-LYS-LEU-ILE-CYS-TYR-THR-SER-VAL-LYS-TRP-ASN.

9. The method according to claim 2 wherein R is the remainder of a peptide having a terminal amino group of the formula (SEQ ID NO: 5)

ARG-ILE-LEU-ALA-VAL-GLU-ARG-TYR-LEU-LYS-ASP-GLN-GLN-
⌐                                                                                     ⌐
LEU-LEU-GLY-ILE-TRP-GLY-CYS-SER-GLY-LYS-LEU-ILE-CYS-
THR-THR-ALA-VAL-PRO-TRP-ASN-ALA-SER.

10. The method according to claim 2 wherein R is the remainder of a peptide having a terminal amino group of the formula (SEQ ID NO: 6)

LYS-ILE-LEU-ALA-VAL-GLU-ARG-TYR-LEU-LYS-ASP-GLN-GLN-
⌐                                                                                     ⌐
LEU-LEU-GLY-ILE-TRP-GLY-CYS-SER-GLY-LYS-LEU-ILE-CYS-
THR-THR-ALA-VAL-PRO-TRP-ASN-ALA-SER-GLY-LYS-LEU-ILE.

11. The method according to claim 2 wherein R is the remainder of a peptide having a terminal amino group of the formula (SEQ ID NO: 7)

ASP-GLN-GLN-LEU-LEU-GLY-ILE-TRP-GLY-
⌐                                                          ⌐
CYS-SER-GLY-LYS-LEU-ILE-CYS-THR-THR-ALA-VAL-PRO-TRP-
ASN.

12. The method according to claim 2 wherein R is the remainder of a peptide having a terminal amino group of the formula (SEQ ID NO: 8)

ASN-GLN-GLN-SER-ARG-TRP-GLY-LEU-GLY-SER-PRO-ASN-
⌐                                                                                   ⌐
CYS-HIS-GLY-PRO-ASP-TRP-ALA-SER-PRO-VAL-CYS-GLN-ARG-
HIS-SER.

13. The method according to claim 2 wherein R is the remainder of a peptide having a terminal amino group of the formula LYS-ILE-GLU-PRO-LEU-GLY-VAL-ALA-PRO-THR-LYS-ALA-
LYS-ARG-ARG-VALVAL-GLN-ARG-GLU-LYS-ARG (SEQ
ID NO: 9).

14. The solid support according to claim 2 wherein $R_1$ is a protein.

15. The solid support according to claim 2 wherein $R_1$ is an enzyme.

16. The solid support according to claim 2 wherein $R_1$ is an antibody.

\* \* \* \* \*